United States Patent [19]
Elliott et al.

[11] Patent Number: 5,929,116
[45] Date of Patent: Jul. 27, 1999

[54] CYCLOPENTENE DERIVATIVES AS ENDOTHELIN RECEPTOR ANTAGONISTS

[75] Inventors: John Duncan Elliott, Wayne; Deborah Lynne Bryan, West Chester, both of Pa.

[73] Assignee: SmithKline Beecham Corporation, Philadelphia, Pa.

[21] Appl. No.: 08/532,778

[22] PCT Filed: Apr. 14, 1994

[86] PCT No.: PCT/US94/04105
§ 371 Date: Oct. 13, 1995
§ 102(e) Date: Oct. 13, 1995

[87] PCT Pub. No.: WO94/24084
PCT Pub. Date: Oct. 27, 1994

[51] Int. Cl.[6] .............................. A01N 37/10; C07C 65/00

[52] U.S. Cl. ............................................ 514/570; 562/473
[58] Field of Search .............................. 562/473; 514/570

[56] References Cited

PUBLICATIONS

K. Kato et al., "New Type of Asymmetric Double Michael Reaction Induced by Chiral Acetal", *Tetrahedron Letters*, vol. 34, No. 31, pp. 4979–4980 (1993).

*Primary Examiner*—Paul J. Killos
*Attorney, Agent, or Firm*—Linda E. Hall; Stephen A. Venetianer; Charles M. Kinzig

[57] ABSTRACT

Novel cyclopentane derivatives are described which are endothelin receptor antagonists.

5 Claims, No Drawings

CYCLOPENTENE DERIVATIVES AS ENDOTHELIN RECEPTOR ANTAGONISTS

FIELD OF INVENTION

The present invention relates to novel cyclopentane derivatives, pharmaceutical compositions containing these compounds and their use as endothelin receptor antagonists.

BACKGROUND

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. Br. J. Pharm. 99: 597–601, 1989 and Clozel and Clozel, Circ. Res., 65: 1193–1200, 1989) coronary vasospasm (Fukuda et al., Eur. J. Pharm. 165: 301–304, 1989 and Lüscher, Circ. 83: 701, 1991) heart failure, proliferation of vascular smooth muscle cells, (Takagi, Biochem & Biophys. Res. Commun.; 168: 537–543, 1990, Bobek et al., Am. J. Physiol. 258: 408–C415, 1990) and atherosclerosis, (Nakaki et al., Biochem. & Biophys. Res. Commun. 158: 880–881, 1989, and Lerman et al., New Eng, J. of Med. 325: 997–1001, 1991). Increased levels of endothelin have been shown after coronary balloon angioplasty (Kadel et al., No. 2491 Circ. 82: 627, 1990).

Further, endothelin has been found to be a potent constrictor of isolated mammalian airway tissue including human bronchus (Uchida et al., Eur. J. of Pharm. 154: 227–228 1988, LaGente, Clin. Exp. Allergy 20: 343–348, 1990; and Springall et al., Lancet, 337: 697–701, 1991). Endothelin may play a role in the pathogenesis of interstetial pulmonary fibrosis and associated pulmonary hypertension, Glard et al., Third International Conference on Endothelin, 1993, p. 34 and ARDS (Adult Respiratory Distress Syndrome), Sanai et al., Supra, p. 112.

Endothelin has been associated with the induction of haemorrhagic and necrotic damage in the gastric mucosa (Whittle et al., Br. J. Pharm. 95: 1011–1013, 1988); Raynaud's phenomenon, Cinniniello et al., Lancet 337: 114–115, 1991); Crohn's Disease and ulcerative colitis, Munch et al., Lancet, Vol. 339, p. 381; Migraine (Edmeads, Headache, Feb. 1991 p 127); Sepsis (Weitzberg et al., Circ. Shock 33: 222–227, 1991; Pittet et al., Ann. Surg. 213: 262–264, 1991), Cyclosporin-induced renal failure or hypertension (Eur. J. Pharmacol., 180: 191–192, 1990, Kidney Int, 37: 1487–1491, 1990) and endotoxin shock and other endotoxin induced diseases (Biochem. Biophys. Res. Commun., 161: 1220–1227, 1989, Acta Physiol. Scand. 137: 317–318, 1989).

Endothelin has also been implicated in preclampsia of pregnancy. Clark et al., Am. J. Obstet. Gynecol. March 1992, p. 962–968; Kamor et al., N. Eng. J. of Med., Nov. 22, 1990, p. 1486–1487; Dekker et al., Eur J. Ob. and Gyn. and Rep. Bio. 40 (1991) 215–220; Schiff et al., Am. J. Ostet. Gynecol. February 1992, p. 624–628; diabetes mellitus, Takahashi et al., Diabetologia (1990) 33: 306–310; and acute vascular rejection following kidney transplant, Watschinger et al., Transplantation Vol. 52, No. 4, pp. 743–746.

Endothelin stimulates both bone resorption and anabolism and may have a role in the coupling of bone remodeling. Tatrai et al. Endocrinology, 131, No. 2, p. 60–607.

Endothelin has been reported to stimulate the transport of sperm in the uterine cavity, Casey et al., J. Clin. Endo and Metabolism, Vol. 74, No. 1, p. 223–225, therefore endothelin antagonists may be useful as male contraceptives. Endothelin modulates the ovarian/menstrual cycle, Kenegsberg, J. of Clin. Endo. and Met., Vol. 74, No. 1, p. 12, and may also play a role in the regulation of penile vascular tone in man, Lau et al., Asia Pacific J. of Pharm., 1991, 6: 287–292 and Tejada et al., J. Amer. Physio. Soc. 1991, H1078–H1085.

Thus, endothelin receptor antagonists would offer a unique approach toward the pharmacotherapy of hypertension, renal failure, cerebrovascular disease, myocardial ischemia, angina, heart failure, asthma, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty and prevention of restenosis, diabetes, preclampsia of pregnancy, bone remodeling, kidney transplant, male contraceptives, infertility and priaprism.

SUMMARY OF THE INVENTION

This invention comprises cyclopentane derivatives represented by Formulas (I), (II) and (III) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, stroke, cerebrovascular vasospasm, myocardial ischemia, angina, heart failure, atherosclerosis and restenosis following balloon angioplasty.

This invention further constitutes a method for antagonizing endothelin receptors in an animal, including humans, which comprises administering to an animal in need thereof an effective amount of a compound of Formula (I), (II) or (III).

DETAILED DESCRIPTION OF THE INVENTION

The compounds of this invention are represented by structural Formulas (I), (II) and (III):

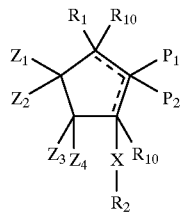

(I)

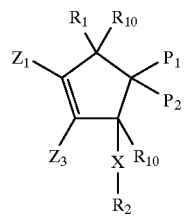

(II)

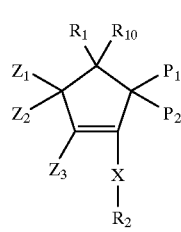

(III)

wherein:

$R_1$ is —$X(CH_2)_n Ar$;

$R_2$ is Ar;

$P_1$ is —$X(CH_2)_n R_8$;

$P_2$ is —$X(CH_2)_n R_8$, or —$XR_9Y$;

$R_3$ and $R_5$ are independently hydrogen, $R_{11}$, OH, $C_{1-8}$alkoxy, $S(O)_q R_{11}$, $N(R_6)_2$, BR, F, I, Cl, $CF_3$, $NHCOR_6$, —$R_{11}CO_2R_7$, —$XR_9$—Y or —$X(CH_2)_n R_8$ wherein each methylene group within —$X(CH_2)_n R_8$ may be unsubstituted or substituted by one or two —$(CH_2)_n Ar$ groups;

$R_4$ is hydrogen, $R_{11}$, OH, $C_{1-5}$alkoxy, $S(O)_q R_{11}$, $N(R_6)_2$, —$X(R_{11})$, Br, F, I, Cl or $NHCOR_6$ wherein the $C_{1-5}$ alkoxy may be unsubstituted or substituted by OH, methoxy or halogen;

$R_6$ is independently hydrogen or $C_{1-4}$ alkyl;

$R_7$ is independently hydrogen, $C_{1-6}$ alkyl or $(CH_2)_n Ar$;

$R_8$ is hydrogen, $R_{11}$, $CO_2R_7$, $PO_3H_2$, $SO_2NR_7R_{11}$, $NR_7SO_2R_{11}$, $P(O)(OH)R_7$, CN, —$C(O)N(R_6)_2$, tetrazole or $OR_6$;

$R_9$ is $C_{1-10}$alkyl, $C_{2-10}$alkenyl or phenyl all of which may be unsubstituted or substituted by one or more OH, $N(R_6)_2$, COOH, >C=O, halogen, or $XC_{1-5}$alkyl;

$R_{10}$ is $R_3$ or $R_4$;

$R_{11}$ is $C_{1-8}$alkyl, $C_{2-8}$alkenyl, $C_{2-8}$alkynyl all of which may be unsubstituted or substituted by one or more OH, $CH_2OH$, $N(R_6)_2$ or halogen;

X is $(CH_2)_n$, O, $NR_6$ or $S(O)_q$;

Y is $CH_3$ or $X(CH_2)_n Ar$;

Ar is:

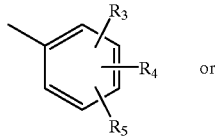 or (a)

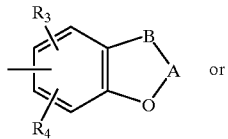 or (b)

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is >C=O, or $[C(R_6)_2]_m$;

B is —$CH_2$— or —O—;

$Z_1$, $Z_2$, $Z_3$, and $Z_4$ are independently hydrogen, $C_{1-8}$alkyl, $C_{2-8}$alkenyl, $C_{2-8}$alkynyl, OH, $C_{1-8}$alkoxy, $S(O)_q C_{1-8}$alkyl, $N(R_6)_2$, Br, F, I, Cl, $NHCOR_6$, —$X(CH_2)_n R_8$, $XR_9Y$, phenyl, benzyl or $C_{3-6}$cycloalkyl wherein the $C_{1-8}$alkyl, $C_{2-8}$alkenyl or $C_{2-8}$alkynyl may be optionally substituted by COOH, OH, $CO(CH_2)_n CH_3$, $CO(CH_2)_n CH_2 N(R_6)_2$, or halogen;

q is zero, one or two;

n is an integer from 0 to 6;

m is 1, 2 or 3;

and the dotted line in Formula (I) indicates the optional presence of a double bond; or a pharmaceutically acceptable salt thereof; provided that when the optional double bond is present there is only one $R_{10}$ and there is no $P_1$ and $P_2$ is not $NR_6R_9Y$;

X is not $NR_6$ and $Z_3$ is not OH or $N(R_6)_2$ in Formula (III);

$Z_1$ and $Z_3$ are not OH, $N(R_6)_2$ or Iodine in Formula (II);

when the optional double bond is present in Formula (I) and X—$R_2$ is attached to the double bond, X is not $NR_6$;

when the optional double bond is present in Formula (I) and $R_1$ is attached directly to the double bond, $R_1$ is not $NR_6 AR$;

when $R_3$, $R_5$, $Z_1$, $Z_2$, or $Z_3$ is $X(CH_2)_n R_8$ and n is not 0, X is oxygen or $NR_6$ when $R_8$ is $OR_6$ or $CO_2H$.

Also included in the invention are pharmaceutically acceptable salts of the active compounds.

All alkyl, alkenyl, alkynyl and alkoxy groups may be straight or branched. The term "halogen"0 is used to mean iodo, fluoro, chloro or bromo. Alkyl groups may be substituted by one or more halogens up to perhalogenation.

The compounds of the present invention may contain one or more asymmetric carbon atoms and may exist in racemic and optically active form. All of these compounds and diastereoisomers are contemplated to be within the scope of the present invention.

Preferred compounds are those wherein $R_1$, is $X(CH_2)_n Ar$, (Ar is (a) or (b)), dihydrobenzofuranyl, benzodioxanyl, cyclohexyl, $C_{1-4}$alkyl; $R_2$ is (a), (b) or indolyl; $R_3$ and $R_5$ are independently hydrogen, OH, $C_{1-5}$alkoxy, halogen, —$OC_{1-4}$alkyl phenyl, $R_{11}CO_2R_7$, $C_{1-4}$alkyl, $N(R_6)_2$, $NH(CO)CH_3$, —X(CH$_2$)$_n$R$_8$, —XR$_9$ pyridyl, SO$_2$NR$_7$R$_{11}$, NR$_7$SO$_2$R$_{11}$, phenyl or S(O)$_p$C$_{1-5}$alkyl; R$_4$ is hydrogen, OH, C$_{1-5}$alkoxy, halogen, C$_{1-4}$alkyl, N(R$_6$)$_2$, NH(CO)CH$_3$ or S(O)$_p$C$_{1-5}$alkyl; Z$_1$, Z$_2$ and Z$_3$ are independently XR$_9$Y, benzyl, hydrogen, OH, C$_{1-5}$alkoxy, —N(R$_6$)$_2$, S(O)$_q$C$_{1-8}$alkyl, NHCOR$_6$, X(CH$_2$)$_n$R$_8$ or halogen; P$_1$ and P$_2$ are independently hydrogen, CO$_2$H or tetrazole; Ar is (a), (b), phenyl, or pyridyl; X is (CH$_2$)$_n$ or oxygen.

The present invention provides compounds of Formula (I), (II) and (III) above.

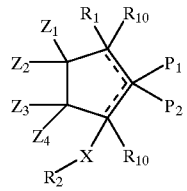
(I)

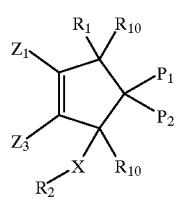
(II)

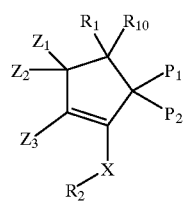
(III)

which can be prepared by a process which comprises:

a) reacting cyclopentene with an equivalent amount of an aryl iodide (R$_2$I, wherein R$_2$ is as defined above) in a suitable solvent such as N,N-dimethylformamide containing potassium acetate and tetra-N-butylammonium chloride in the presence of a catalytic quantity of palladium acetate at 60–100° C. under an inert atmosphere such as argon to provide a compound of Formula (4).

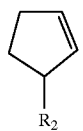
(4)

Further treatment of compound (4) with an equivalent amount of an aryl iodide (R$_1$I, wherein R$_1$ is as defined above) in a suitable solvent such as N,N-dimethylformamide containing potassium acetate and tetra-N-butylammonium chloride in the presence of a catalytic quantity of palladium acetate at 60–100° C. under an inert atmosphere such as argon affords compounds of Formula (5).

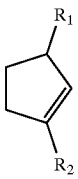
(5)

Reaction of compounds of Formula (5) with paraformaldehyde in the presence of diethylaluminum chloride in a solvent such as dichloromethane affords alcohols of structure (6).

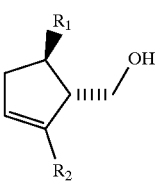
(6)

Reduction of compounds of structure (6) with hydrogen gas at atmospheric pressure in the presence of a suitable catalyst such as 5–10% palladium on charcoal in a solvent such as ethyl acetate affords cyclopentanes of Formula (7).

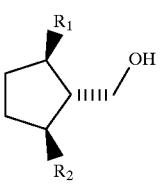
(7)

Oxidation of alcohols of Formula (7) with Jones reagent in a suitable solvent such as acetone affords compounds of Formula (I), (II) and (III) wherein Z$_1$, Z$_2$, Z$_3$, Z$_4$, R$_{10}$ and P$_2$=H, P$_1$=CO$_2$H and X=(CH$_2$)$_n$, n=0, and the optional double bond is not present, ie., structures of Formula (8).

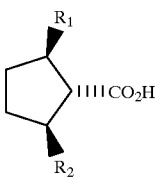
(8)

b) Alternatively, oxidation of compounds of Formula (6) with an oxidant such as pyridinium dichromate in a suitable solvent such as N,N-dimethylformamide, followed by esterification with a suitable alcohol, YOH, wherein Y is C$_{1-5}$alkyl, in the presence of an acid such as sulfuric affords esters of Formula (9).

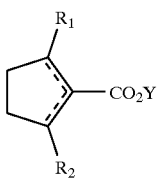

(9)

Saponification of esters of Formula (9) using aqueous sodium hydroxide solution in a suitable solvent such as methanol, followed by chromatographic separation of the double bond regioisomers affords compounds of Formula (I), (II) and (III) wherein $Z_1$, $Z_2$, $Z_3$, $Z_4$=H, $P_2$=$CO_2$H, the optional double bond is present, X=$(CH_2)_n$, n=0, there is only one $R_{10}$ and there is no $P_1$, i.e., structures of Formula (10).

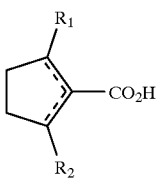

(10)

c) As a further alternative chromatographic separation of the double bond regioisomers of esters of Formula (9) affords compounds of Formula (11)

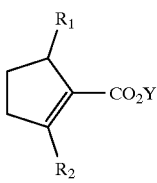

(11)

Deprotonation of esters of Formula (11) with a base such as lithium di-isopropylamide in a suitable solvent such as tetrahydrofuran under an inert atmosphere such as argon at low (−40° C. to −78° C.) temperature followed by quenching with a suitable electrophile: $R_8(CH_2)_nX$-Hal or $YR_9X$-Hal wherein X=$(CH_2)_n$ and Hal is an halogen, e.g., Br, I and $R_8$ and $R_9$ are as defined above, affords compounds of structure (12).

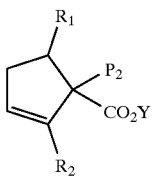

(12)

d) As a further alternative, esterification of acids of structure (8) with a suitable alcohol, YOH, wherein Y is $C_{1-5}$alkyl, in the presence of an acid such as sulfuric affords esters of Formula (13).

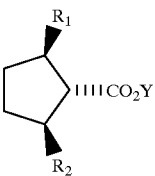

(13)

Deprotonation of esters of Formula (13) with a base such as lithium di-isopropylamide in a suitable solvent such as tetrahydrofuran under an inert atmosphere such as argon at low (−40° C. to −78° C. temperature followed by quenching with phenylselenyl chloride and subsequent oxidation with aqueous hydrogen peroxide affords esters of Formula (12) described above.

With appropriate manipulation and protection of any chemical functionalities, synthesis of the remaining compounds of the Formulas (I), (II) and (III) is accomplished by methods analogous to those above and to those described in the Experimental section.

In order to use a compound of the Formulae (I), (II) and (III) or a pharmaceutically acceptable salt thereof for the treatment of humans and other mammals it is normally formulated in accordance with standard pharmaceutical practice as a pharmaceutical composition.

Compounds of Formula (I), (II) and (III) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I), (II) and (III) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formulas (I), (II) and (III) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I), (II) and (III) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formulas (I), (II) and (III).

The daily dosage regimen for oral administration is suitably about 0.01 mg/Kg to 40 mg/Kg, of a compound of Formulas (I), (II) and (III) or a pharmaceutically acceptable salt thereof calculated as the free acid. The daily dosage regimen for parenteral administration is suitably about 0.001 mg/Kg to 40 mg/Kg, of a compound of the Formulas (I), (II) and (III) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formulas (I), (II) and (III) are demonstrated by the following tests:

I. Binding Assay

A) Membrane Preparation

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motor-driven homogenizer. The homogenates were filtered through cheesecloth and centrifuged at 20,000 x g for 10 minutes at 4° C. The supernatant was removed and centrifuged at 40,000 xg for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 mg of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5mM EDTA, pH 7.5 at 4° C. in 15 ml volume for ~6 gm of mesenteric artery bed. The homogenate was strained through cheesecloth and centrifuged at 2,000 xg for 10 min. at 4° C. The supernatant was removed and centrifuged at 40,000 xg for 30 min. at 4° C. The resulting pellet was resuspended as explained above for cerebellum and kidney cortex. Approximately 10 mg of membrane protein was used for each tube-in binding experiments.

B) [$^{125}$I]ET-1 Binding Protocol

[$^{125}$I]ET-1 binding to membranes from rat cerebellum (2–5 mg protein/assay tube) or kidney cortex (3–8 mg protein/assay tube) were measured after 60 minutes incubation at 30° C. in 50 mM Tris HCl, 10 mM $MgCl_2$, 0.05% BSA, pH 7.5 buffer in a total volume of 100 ml. Membrane protein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM $MgCl_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%. $IC_{50}$'s for the compounds of this invention range from 0.1 nm to 50 μm.

II. In Vitro Vascular Smooth Muscle Activity

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; $KH_2PO_4$, 1.2; $MgSO_4$, 1.2; $CaCl_2$, 2.5; $NaHCO_3$, 25.0; and dextrose, 11.0. Tissue bath solutions are maintained at 37° C. and aerated continuously with 95% $O_2$/5% $CO_2$. Resting tensions of aorta are maintained at 1 g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist. ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean ± S.E.M. Dissociation constants (Kb) of competitive antagonists were determined by the standard method of Arunlakshana and Schild. The potency range for compounds of this invention range from 0.1 nM to 50 μm.

The following examples are illustrative and are not limiting of the compounds of this invention.

EXAMPLE 1

(1RS,2RS,3SR)-1,3 bis(4-methoxyphenyl) cyclopentane-2-carboxylic acid a) 1,3-Bis(4-methoxyphenyl)cyclopent-1-ene A mixture of cyclopentene (2.72 g, 40 mmol), p-iodoanisole (21.53 g, 92 mmol), palladium acetate (224.5 mg, 1 mmol), tetrabutylammonium chloride (25.57 g, 92 mmol), potassium acetate (27.10 g, 276 mmol) in DMF (140 ml) was stirred at room temperature for 1 hour, then the reaction was heated to 80° and stirred vigorously for 3 days. The reaction mixture was partitioned between hexane and $H_2O$, the aqueous layer separated and further extracted with hexane (3×) and the combined extracts were washed with 10% $NH_4Cl$, $H_2O$ (2×), 1N HCl, 5% $Na_2S_2O_3$, 5% $NaHCO_3$, water and brine. After charcoal treatment, drying ($MgSO_4$), filtration, and evaporation gave a brown solid (13 g). The crude product was recrystallized from EtOH to give a first crop of (a) (6.87 g, 61%) contaminated only slightly with biphenyl.

b) (3RS,4SR)-2,4-Bis(4-methoxyphenyl)-3-hydroxymethylcyclopent-1-ene

To a solution of 1,3-Bis(4-methoxyphenyl)-cyclopent-1-ene (280 mg, 1 mmol) and paraformaldehyde (120 mg, 4 mmol) in dry methylene chloride (2 ml) was added dropwise diethylaluminum chloride (3.6 ml of a 1M solution in hexanes, 3.6 mmol) at room temperature and the reaction stirred for 3 hrs. The temperature was lowered to −15° and the reaction quenched by addition of 6N HCl dropwise. The mixture was diluted with water and extracted with $CH_2Cl_2$. The combined extracts were washed with 5% $NaHCO_3$ and brine, dried ($MgSO_4$), and filtered. Evaporation of the solvent under reduced pressure afforded crude purple oil (484 mg). Silica gel chromatography (eluant 30% EtOAc/hexanes) gave (b) as a colorless oil (188 mg, 60%).

c (1RS,2RS,3SR)-1,3-bis(4,-methoxyphenyl)-2-hydroxymethylcyclopentane

Crude (3RS,4RS)-2,4-bis(4-methoxyphenyl)-3-hydroxymethylcyclopent-1-ene was stirred under 1 Atm of $H_2$ in EtOAc (3 ml) with 10% Pd/C catalyst (38 mg) for 4 hrs. The reaction mixture was diluted with EtOAc and filtered to remove the catalyst. The crude oil was chromatographed on silica gel to afford 300 mg of (c). (48% for 2 steps).

d) (1RS,2RS,3SR)-1,3 bis(4-methoxyphenyl)-cyclopentane-2-carboxylic acid

To a solution of (1RS,2RS,3SR)-1,3-bis(4-methoxyphenyl)-2-hydroxymethylcyclopentane (91 mg, 0.29 mmol) in acetone (3 ml) was added dropwise with vigorous stirring at room temperature Jones reagent until a persistant orange color remained. The reaction was quenched with addition of 1 to 2 drops of isopropanol and stirred until the solution turned green. The mixture was diluted with acetone and the salts removed by filtration. The solution was evaporated under reduced pressure and the residue taken up with EtOAc. After drying ($MgSO_4$ anhyd.), filtration and evaporation afforded the title compound as a tan solid (76 mg, 80%). Recrystallization from EtOAc/hexanes gave white solid (22.7 mg). mp 153–155°

MS (DCI $CH_4$) m/e: 355 $(M+C_2H_5)^+$, 337.1 $(M+C_2H_5-H_2O)+$, 327 $(M+H)+$, 326.1 M+, 309.1 $(M+H-H_2O)+$

Anal. Calc. for $C_{20}H_{22}O_4$. 1/8 $H_2O$: C,73.09; H, 6.80. Found: C, 73.03; H, 7.04.

EXAMPLE 2

Formulations for pharmaceutical use incorporating compounds of the present invention can be prepared in various forms and with numerous excipients. Examples of such formulations are given below.

Inhalant Formulation

A compound of Formulas I, II, or III, (1 mg to 100 mg) is aerosolized from a metered dose inhaler to deliver the desired amount of drug per use.

| Tablets/Ingredients | Per Tablet |
| --- | --- |
| 1. Active ingredient (Cpd of Form; I, II or III) | 40 mg |
| 2. Corn Starch | 20 mg |
| 3. Alginic acid | 20 mg |
| 4. Sodium alginate | 20 mg |
| 5. Mg stearate | 1.3 mg |
| | 2.3 mg |

Procedure for Tablets

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its converion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of Formulas I, II or III in polyethylene glycol with heating. This solution is then diluted with water for injections Ph Eur. (to 100 ml). The solution is then steriled by filtration through a 0.22 micron membrane filter and sealed in sterile containers.

What is claimed is:

1. The compounds of this invention are represented by structural Formula (I), (II) or (III):

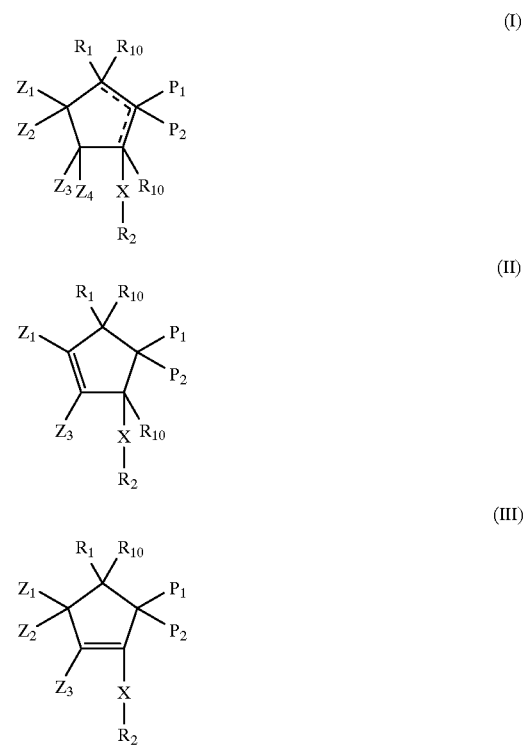

wherein:

$R_1$ is $—X(CH_2)_nAr$;

$R_2$ is Ar;

$P_1$ is $—X(CH_2)_nR_8$;

$P_2$ is $—X(CH_2)_nR_8$, or $—XR_9Y$;

$R_3$ and $R_5$ are independently hydrogen, $R_{11}$, OH, $C_{1-8}$alkoxy, $S(O)_qR_{11}$, $N(R_6)_2$, BR, F, I, Cl, $CF_3$, $NHCOR_6$, $—R_{11}CO_2R_7$, $—XR_9—Y$ or $—X(CH_2)_nR_8$ wherein each methylene group within $—X(CH_2)_nR_8$ may be unsubstituted or substituted by one or two $—(CH_2)_nAr$ groups;

$R_4$ is hydrogen, $R_{11}$, OH, $C_{1-5}$alkoxy, $S(O)_qR_{11}$, $N(R_6)_2$, —$X(R_{11})$, Br, F, I, Cl or $NHCOR_6$ wherein the $C_{1-5}$ alkoxy may be unsubstituted or substituted by OH, methoxy or halogen;

$R_6$ is independently hydrogen or $C_{1-4}$ alkyl;

$R_7$ is independently hydrogen, $C_{1-6}$ alkyl or $(CH_2)_nAr$;

$R_8$ is hydrogen, $R_{11}$, $CO_2R_7$, $PO_3H_2$, $SO_2NR_7R_{11}$, $NR_7SO_2R_{11}$, $P(O)(OH)R_7$, CN, —$C(O)N(R_6)_2$, tetrazole or $OR_6$;

$R_9$ is $C_{1-10}$alkyl, $C_{2-10}$alkenyl or phenyl all of which may be unsubstituted or substituted by one or more OH, $N(R_6)_2$, COOH, >C=O, halogen, or $XC_{1-5}$alkyl;

$R_{10}$ is $R_3$ or $R_4$;

$R_{11}$ is $C_{1-8}$alkyl, $C_{2-8}$alkenyl, $C_{2-8}$alkynyl all of which may be unsubstituted or substituted by one or more OH, $CH_2OH$, $N(R_6)_2$ or halogen;

X is $(CH_2)_n$, O, $NR_6$ or $S(O)_q$;

Y is $CH_3$ or $X(CH_2)_nAr$;

Ar is:

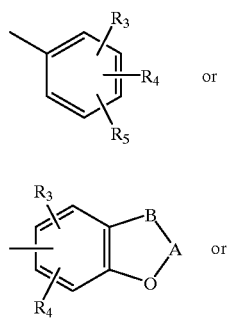

(a)

(b)

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is >C=O, or $[C(R_6)_2]_m$;

B is —$CH_2$— or —O—;

$Z_1$, $Z_2$, $Z_3$, and $Z_4$ are independently hydrogen, $C_{1-8}$alkyl, $C_{2-8}$alkenyl, $C_{2-8}$alkynyl, OH, $C_{1-8}$alkoxy, $S(O)_qC_{1-8}$alkyl, $N(R_6)_2$, Br, F, I, Cl, $NHCOR_6$, —$X(CH_2)_nR_8$, $XR_9Y$, phenyl, benzyl or $C_{3-6}$cycloalkyl wherein the $C_{1-8}$alkyl, $C_{2-8}$alkenyl or $C_{2-8}$alkynyl may be optionally substituted by COOH, OH, $CO(CH_2)_nCH_3$, $CO(CH_2)_nCH_2N(R_6)_2$, or halogen;

q is zero, one or two;

n is an integer from 0 to 6;

m is 1, 2 or 3;

and the dotted line in Formula (I) indicates the optional presence of a double bond; or a pharmaceutically acceptable salt thereof; provided that when the optional double bond is present there is only one $R_{10}$ and there is no $P_1$ and $P_2$ is not $NR_6R_9Y$;

X is not $NR_6$ and $Z_3$ is not OH or $N(R_6)_2$ in Formula (III);

$Z_1$ and $Z_3$ are not OH, $N(R_6)_2$ or Iodine in Formula (II);

when the optional double bond is present in Formula (I) and X—$R_2$ is attached to the double bond, X is not $NR_6$;

when the optional double bond is present in Formula (I) and $R_1$ is attached directly to the double bond, $R_1$ is not $NR_6AR$;

when $R_3$, $R_5$, $Z_1$, $Z_2$, or $Z_3$ is $X(CH_2)_nR_8$ and n is not 0, X is oxygen or $NR_6$ when $R_8$ is $OR_6$ or $CO_2H$.

2. A compound of claim 1 wherein R1 is X $(CH_2)_nAr$, (Ar is (a) or (b)), dihydrobenzofuranyl, benzodioxanyl, cyclohexyl, $C_{1-4}$alkyl; $R_2$ is (a), (b) or indolyl; $R_3$ and $R_5$ are independently hydrogen, OH, $C_{1-5}$alkoxy, halogen, —$OC_{1-4}$alkyl phenyl, $R_{11}CO_2R_7$, $C_{1-4}$alkyl, $N(R_6)_2$, $NH(CO)CH_3$, —$(CH_2)_nR_8$, —$XR_9$ pyridyl, $SO_2NR_7R_{11}$, $NR_7SO_2R_{11}$, phenyl or $S(O)_pC_{1-5}$alkyl; $R_4$ is hydrogen, OH, $C_{1-5}$alkoxy, halogen, $C_{1-4}$alkyl, $N(R_6)_2$, $NH(CO)CH_3$ or $S(O)_pC_{1-5}$alkyl; $Z_1$, $Z_2$ and $Z_3$ are independently $XR_9Y$, benzyl, hydrogen, OH, $C_{1-5}$alkoxy, —$N(R_6)_2$, $S(O)_qC_{1-8}$alkyl, $NHCOR_6$, $X(CH_2)_nR_8$ or halogen; $P_1$ and $P_2$ are independently hydrogen, CO2H or tetrazole; Ar is (a), (b), phenyl, or pyridyl; X is $(CH_2)$ or oxygen.

3. A pharmaceutical composition comprising a compound of claim 1 and a pharmaceutically acceptable carrier.

4. A method of antagonizing endothelin receptors which comprises administering to a subject in need thereof, an effective amount to antagonize endothelin receptors of a compound of claim 1.

5. A method of treating hypertension, renal failure or cerebrovascular disease which comprises administering to a subject in need thereof, an effective amount of a compound of claim 1.

* * * * *